United States Patent
Hamada

(10) Patent No.: US 8,315,441 B2
(45) Date of Patent: Nov. 20, 2012

(54) MASQUERADE DETECTION SYSTEM, MASQUERADE DETECTION METHOD AND MASQUERADE DETECTION PROGRAM

(75) Inventor: Yasushi Hamada, Tokyo (JP)

(73) Assignee: NEC Corporation, Tokyo (JP)

( * ) Notice: Subject to any disclaimer, the term of this patent is extended or adjusted under 35 U.S.C. 154(b) by 536 days.

(21) Appl. No.: 12/602,930

(22) PCT Filed: Jun. 17, 2008

(86) PCT No.: PCT/JP2008/061046
§ 371 (c)(1),
(2), (4) Date: Dec. 3, 2009

(87) PCT Pub. No.: WO2009/004916
PCT Pub. Date: Jan. 8, 2009

(65) Prior Publication Data
US 2010/0177939 A1    Jul. 15, 2010

(30) Foreign Application Priority Data

Jun. 29, 2007 (JP) ................................. 2007-173302

(51) Int. Cl.
*G06K 9/62* (2006.01)
(52) U.S. Cl. ........................................................ 382/118
(58) Field of Classification Search .................. None
See application file for complete search history.

(56) References Cited

U.S. PATENT DOCUMENTS

2003/0206645 A1*  11/2003  Okazaki et al. ............... 382/117
2004/0240711 A1*  12/2004  Hamza et al. ................. 382/118
2006/0093183 A1*   5/2006  Hosoi ............................ 382/103
2007/0047775 A1*   3/2007  Okubo ........................... 382/118
2007/0252674 A1*  11/2007  Nelson et al. ................. 340/5.53

FOREIGN PATENT DOCUMENTS

| JP | 7-302327 A | 11/1995 |
| JP | 2003178306 A | 6/2003 |
| JP | 2004192378 A | 7/2004 |
| JP | 2004362079 A | 12/2004 |
| JP | 2006309529 A | 11/2006 |
| JP | 2007004530 A | 1/2007 |

OTHER PUBLICATIONS

English translation of JP 2006-309529, published on Nov. 9, 2006, detailed description portion only, pp. 1-9.*
International Search Report for PCT/JP2008/061046 mailed Jul. 22, 2008.

(Continued)

*Primary Examiner* — Brian P Werner

(57) ABSTRACT

To provide a masquerade detection system which can detect a masquerade using a photograph, a picture or the like, without using an additional device other than an image picking-up device. A masquerade detection method includes an image conversion step in which an image conversion from one flat plane to the other flat plane is carried out from a first image of an examining object picked up from a first angle into a second image of an examining object picked up from a second angle different from the first angle to generate a converted image, and a masquerade judging step in which the converted image and the second image are entirely or partially compared with each other and, if a compared result satisfies a predetermined condition, an attempt to do a masquerade is judged.

39 Claims, 5 Drawing Sheets

OTHER PUBLICATIONS

K. Fukui et al, "Facial Feature Point Extraction Method Based on Combination of Shape Extraction and Pattern Matching", Transactions of The Institute of Electronics, Information and Conmmunication Engineers, D-II, vol. J80-D-II, No. 8, pp. 2170-2177, Aug. 1997.

R. Sukthankar et al., "Smarter Presentations: Exploiting Homography in Camera-Projector Systems", Proceedings of International Conference on Computer Vision, vol. 1, pp. 247-223, 2001.

* cited by examiner

MASQUERADE DETECTION SYSTEM, MASQUERADE DETECTION METHOD AND MASQUERADE DETECTION PROGRAM

The present application is the National Phase of PCT/JP2008/061046, filed Jun. 17, 2008, which claims priority based on Japanese Patent Application No. 2007-173302 filed on Jun. 29, 2007, the entire disclosure of which is incorporated herein.

TECHNICAL FIELD

The present invention relates to a masquerade detection system, a masquerade detection method, and a masquerade detection program, and particularly, to a masquerade detection system, a masquerade detection method, and a masquerade detection program which can detect a masquerade when a personal authentication is performed according to a head including a part or all of a face.

BACKGROUND ART

In a face authentication system as being a system for a personal authentication, a technique to detect a masquerade that uses a photograph or the like has been considered.

For example, a personal authentication device described in Patent Document 1 excludes a masquerade depending on a degree of similarity of facial images under different illumination environments created by changing the illumination environment using an illumination lamp. Also, a masquerade detection device described in Patent Document 1 excludes a masquerade by comparing distance information obtained by using a distance detection device with face depth information stored in advance. Further, the masquerade detection device described in Patent Document 1 excludes a masquerade by: obtaining various images in which a user's face is picked up from many angles: and authenticating the user's action by using a contributing ratio in the degree of the variation of images obtained by principal component analysis.

A biometric collation device described in Patent Document 2 eliminates a masquerade that uses a photograph by: generating three-dimensional information of a user by using a plurality of picked up images of the user and picked up angles therewith; and collating the information with a three-dimensional shape of a face of an authenticated person stored in advance.

Patent Document 1: Japanese Unexamined Patent Publication 2003-178306

Patent Document 2: Japanese Unexamined Patent Publication 2004-362079

DISCLOSURE OF THE INVENTION

Problems to be Solved by the Invention

A problem of the techniques described above is that an additional device is required for detecting the masquerade, other than a face image picking-up device used for an authentication. For instance, a controllable external illumination lamp is required for creating different illumination environments, and an exclusive distance detection device is required for measuring the distance.

An object of the present invention is to provide a masquerade detection system which can detect a masquerade that uses a photograph, a picture or the like, without using an additional device other than an image picking-up device.

Means for Solving the Problems

In order to achieve the above-described object, a masquerade detection method of the present invention is a method to detect a masquerade based on an image containing an examining object, the method including:

converting an image containing the examining object picked up from one angle into an image of the examining object picked up from other angle different from the one angle, by performing an image conversion from one flat plane to other flat plane;

comparing the converted image with an image containing the examining object picked up from the other angle; and judging that the examining object is attempting to do a masquerade when the converted image and the image containing the examining object picked up from the other angle are matched.

Effects of the Invention

According to the present invention, a masquerade can be detected without using an additional device other than an image picking-up device.

Best Mode for Carrying Out the Invention

Next, a masquerade detection device 1 according to an exemplary embodiment of the invention will be described in detail by referring to accompanying drawings.

First, a basic principle in the exemplary embodiment of the invention will be described. When a person is passing through a checkpoint by attempting to do a masquerade using a flat photograph of an examining object, and when a detection of the masquerade is performed by using an image obtained by picking up the flat photograph, a converted image which is converted from an image obtained by picking up the flat photograph (examining object) from one angle by performing an image conversion from one flat plane to other flat plane is expected to be matched with an image which is obtained by picking up the flat photograph (examining object) from other angle different from the one angle.

On the other hand, when the detection of the masquerade is performed by using an image obtained by picking up an examining object having an uneven shaped surface, or an examining object having a stereoscopic shape, a converted image which is converted from an image obtained by picking up the examining object having an uneven shaped surface or a stereoscopic shape from one angle by performing an image conversion from one flat plane to other flat plane is not expected to be matched with an image which is obtained by picking up the examining object having an uneven shaped surface or a stereoscopic shape from other angle different from the one angle, when compared.

A masquerade detection system according to an exemplary embodiment of the invention detects the masquerade that uses the flat photograph based on the above described principle, and the system includes: an image conversion device (an image conversion unit 103) which converts, by performing an image conversion from one flat plane to other flat plane, an image containing the examining object picked-up from one angle to an image which is picked-up from other angle different from the one angle; and a judging device (a masquerade judging unit 105) which compares the converted image with an image containing the examining object picked up from the other angle, and judges that the examining object is attempting to do a masquerade when the converted image and the image containing the examining object picked up from the other angle are matched.

In the exemplary embodiment of the invention, when detecting the masquerade based on the image containing the examining object, an image containing the examining object picked up from one angle is converted, by performing an image conversion from one flat plane to other flat plane, into an image picked up from other angle different from the one angle; the converted image is compared with an image containing the examining object picked up from the other angle; and the examining object is judged as attempting to do a masquerade when the converted image and the image containing the examining object picked up from the other angle are matched.

Next, a specific example of the masquerade detection system according to the exemplary embodiment of the invention will be explained as a first exemplary embodiment according to FIG. 1 to FIG. 4.

First Exemplary Embodiment

The masquerade detection system 1 according to the first exemplary embodiment of the invention includes an image conversion unit 103 and a masquerade judging unit 105 as a basic configuration as shown in FIG. 1. In an example shown in FIG. 1, a data processor (computer) 101 operated by a program control is used, and the image conversion unit 103 and the masquerade judging unit 105 are realized by causing the data processor 101 to execute the program. Also, the image conversion unit 103 includes an examining object extracting unit 101 and a first portion extracting unit 102. Further, the masquerade judging unit 105 includes a second portion extracting unit 104. Furthermore, the data processor 101 includes a measurement device 200 which measures the examining object.

The measurement device 200 picks up the examining object and outputs the picked up image data to the data processor 100, and the measurement device 200 includes an image picking-up unit 201. The image picking-up unit 201 is configured with a digital camera, for example, and in this case, position and direction of the examining object with respect to the image picking-up unit 201 is fixed.

When the examining object is a person for example, the measurement device 200 prompts the person to change his/her posture to be picked up, then picks up the examining object whose posture is changed, and outputs the picked up image data to the data processor 100.

The image data of the examining object, outputted from the measurement device 200 to the data processor 100 at an initial state with which the position and direction of the examining object with respect to the image picking-up unit 201 is fixed, is the image picked up from one angle (hereinafter, referred to as a first angle image). Further, the image data of the examining object, outputted from the measurement device 200 to the data processor 100 when the examining object is picked up after the position thereof is changed from the initial state, is the image picked up from other angle different from the one angle (hereinafter, referred to as a second angle image). In the first angle image and the second angle image, directions of the examining object are different with respect to the image picking-up unit 201.

The examining object extracting unit 101 extracts images of the examining object from the first angle image and the second angle image picked up by the image picking-up unit 201, respectively. Accordingly, the images of the examining object extracted by the examining object extracting unit 101 includes two kinds of images corresponding to the first angle image and the second angle image respectively. Here, the image generated by extracting the examining object from the first angle image is referred to as a first angle examining object image, and the image generated by extracting the examining object from the second angle image is referred to as a second angle examining object image.

The first portion extracting unit 102 extracts images containing first portions from the first angle examining object image and the second angle examining object image extracted by the examining object extracting unit 101, respectively. Accordingly, the images extracted by the first portion extracting unit 102 includes two kinds of images, an image containing the first portion extracted from the first angle examining object image and an image containing the first portion extracted from the second angle examining object image.

The image conversion unit 103 generates a converted image which is converted from the first angle examining object image by performing an image conversion from one flat plane to other flat plane, by using the image containing the first portion extracted from the first angle examining object image by the first portion extracting unit 102. This converted image corresponds to the second angle examining object image. Specifically, the image conversion unit 103 compares the image containing the first portion extracted from the first angle examining object image with the image containing the first portion extracted from the second angle examining object image (picked up image), converts the first angle examining object image by performing an image conversion from one flat plane to other flat plane such that the corresponding first portions are to be matched, and generates the second angle examining object image (image-converted image). At a time when the processing of the image conversion unit 103 is completed, there are two kinds of second angle examining object images, i.e., the second angle examining object image (image-converted image) which is generated through the image conversion by the image conversion unit 103, and the second angle examining object image (picked up image) which is picked up by the image picking-up unit 201 with the posture of the examining object being changed. Here, the second angle examining object image (image-converted image) which is generated, by performing an image conversion from one flat plane to other flat plane, from the first angle examining object image by the image conversion unit 103 is referred to as a converted image. The processing of the image conversion will be described later.

The second portion extracting unit 104 extracts the second portions from the converted image (image-converted image) and the second angle examining object image (picked up image) respectively. Specifically, the second portion extracting unit 104 extracts the second portions different from the first portions from the converted image (image-converted image) generated by the image conversion unit 103 and the second angle examining object image (picked up image), respectively.

The masquerade judging unit 105 compares the second angle examining object image (image-converted image) generated through the image conversion with the second angle examining object image (picked up image), and in particular, compares the images of areas containing the second portions with each other in the two images, to obtain the degree of similarity. The masquerade judging unit 105 judges that it is a masquerade that uses the flat photograph when the degree of similarity between the two images is high, that is, when the images of the second portions are matched. Meanwhile, the masquerade judging unit 105 judges that it is not a masquerade that uses the flat photograph, when the degree of similarity between the two images is low, that is, when the images of the second portions are not matched. Here, "match" is used for such a case in which a comparison result satisfies a prescribed condition, in addition to a case in which the two images are completely coincided.

Next, an entire operation of the masquerade detection device 1 according to the first exemplary embodiment of the invention will be explained in detail by referring to flowcharts shown in FIG. 1 and FIG. 2.

First, the examining object extracting unit 101 extracts the image of the examining object from the first angle image picked up by the image picking-up unit 201 (step S101 in FIG. 2). When the examining object extracted by the examining object extracting unit 101 is a face of a person for example, the examining object extracting unit 101 extracts a facial image by extracting a skin-colored area in the facial image of the person, for example (skin color detection).

Then, the first portion extracting unit 102 extracts the image containing the first portion from the first angle examining object image (step S102 in FIG. 2). When the examining object is, for example, a face of a person, the first portion extracted by the first portion extracting unit 102 is configured with a combination of a plurality of facial parts, which can be extracted stably. The image containing the first portion may be, for example, an image containing four or more points from among center points or contour points of: both eyes; eyebrows; a mouth; or nostrils. Also, the image containing the first portion may be an image containing both center points of eyes and both endpoints of a mouth. Further, the image containing the first portion may be an image showing: both center points of eyes; a center point of a mouth; a size of the mouth; and a slope of the mouth. The image of those portions may be extracted by using a pixel at which the brightness value of the image varies drastically.

Also, the image may be extracted in such a manner that the first portion extracting unit 102 stores the image of the first portion to be extracted, or, receives the image of the first portion to be extracted from outside at the time of extracting, then applies the image of the first portion to be extracted to the examining object image, and extracts the corresponding portion, as described in a document (Kazuhiro Fukui, Osamu Yamaguchi, "Facial Feature Point Extraction Method Based on Combination of Shape Extraction and Pattern Matching," Transactions of The Institute of Electronics, Information and Communication Engineers, D-II, Vol. J80-D-II, No. 8, pp. 2170-2177, 1997)

The first portion to be extracted by the first portion extracting unit 102 is desirably a portion which can be extracted stably even when the posture (direction) of the examining object is changed when being picked up. Therefore, a portion whose appearance in the image changes with the change in posture of the examining object, such as a nose tip, is desired to be avoided.

After picking up the examining object image from the first angle, the object to be picked up is prompted to change the posture, and the image picking-up unit 201 picks up the examining object from the second angle. The examining object extracting unit 101 extracts the examining object image from the picked up image containing the second angle examining object in the same manner as step S101 (step S103). The masquerade can be judged with a single image picking-up unit 201 by picking up the second angle image because of the postural change of the examining object.

The first portion extracting unit 102 extracts an image containing the first portion from the second angle image in the same manner as step S102 (step S104).

The image conversion unit 103 compares the image containing the first portion extracted from the first angle examining object image with the image containing the first portion extracted from the second angle examining object image, and obtains an image converting method with which, by performing an image conversion from one flat plane to other flat plane, the first angle image is converted to an image corresponding to the second angle image obtained from the picked up image, such that the corresponding images of the first portions are to be matched (step S105). The image conversion unit 103 generates the converted image by converting the first angle image to the second angle image by using the obtained image converting method (step S106). For the image conversion from one flat plane to the other flat plane processed by the image conversion unit 103, a homography matrix may be used, as described in a document (R. Sukthankar, R. G. Stocktom, M. D. Mullin, "Smarter Presentations: Exploiting Homography in Camera-Projector Systems," Proceedings of International Conference on Computer Vision, Vol. 1, pp. 247-253, 2001). The image converting method is obtained by determining a parameter of the homography matrix by using four or more corresponding parts in the first portions of the first angle examining object image and the second angle examining object image. When an effect of the perspective projection can be ignorable as in the case that the camera and the examining object are widely separated, the image conversion may be performed by using affine transformation. In such a case, the image converting method is obtained by determining a parameter of the affine transformation by using three or more parts in the first portion. The three parts in the first portions are selected so as not to form a straight line on the image. Also, it is desirable that respective parts in the first portions are separated from each other for a excellently precise image conversion. Further, the image converting method may be obtained by using the image of the first portion and the image of the first portion other than the examining object when comparing the image of the first portion of the examining object picked up from the one angle with the image of the first portion of the examining object picked up from the other angle. Furthermore, when obtaining the image converting method, the images of second portions different from the first portions may be compared. The "second portion" will be described later.

The second portion extracting unit 104 extracts areas containing second portions different from the first portions from the first angle examining object image which is obtained by image conversion (image-converted image) and the second angle examining object image (picked up image) respectively. The second portion extracted by the second portion extracting unit 104 is configured by the parts whose appearance in the image change significantly between the two different examining object images if the examining object is not the flat photograph. The image of the second portion may be the image of a facial contour for example. Also, the second portion may be the image expressing a distance between an oral end and the facial contour for example. Since each cheek has an anteroposterior widening, the appearance of the facial contour varies significantly depending on a facing direction of the face in a case of the real person. Further, the image of the second portion may be the image of a nose for example. Since the nose is a largely protruded part, the appearance varies significantly depending on a facing direction of the face in a case of the real person. Furthermore, as an image containing the second portion, the image of the entire examining object may be used. With this, processing load can be reduced by eliminating the processing executed by the second portion extracting unit 104.

The masquerade judging unit 105 compares the images of areas containing the second portions extracted respectively from the converted image (image-converted image) and the second angle examining object image (picked up image), to obtain the degree of similarity of those images (step S107). For obtaining the degree of similarity, the normalized correlation value may be used. Then, the masquerade judging unit 105 compares the degree of similarity with a prescribed threshold value (step S108). In the case of the masquerade that uses the photograph, the images containing the second portions (facial contours 33a and 33b, for example) which are extracted respectively from the converted image (image-converted image) 31 obtained by converting the first angle examining object image 30 and the second angle examining object image (picked up image) 32 are matched as shown in FIG. 3. Accordingly, the masquerade judging unit 105 determines that the images are matched when the degree of similarity is greater than the prescribed threshold value (Yes in step S108), and judges that the examining object is attempting to do the masquerade by using the flat photograph (step S109). Here, in the processing for judging the masquerade, when the masquerade judging unit 105 compares the images containing the second portions, images of the entire examining object containing the second portion may be used to be compared. Also, the images containing the second portions may be compared by using the image containing the cheek part between the mouth and the facial contour as the image of the second portion by setting the length of the cheek part as a reference. Further, the images containing the second portions may be compared by setting a difference in the luminance values of the images as a reference.

With the facial image of the real person, the images of the areas containing the second portions (facial contours 43a and 43b, for example) which are extracted respectively from the converted image (image-converted image) 41 obtained by converting the first angle examining object image 40 and the second angle examining object image (picked up image) 42 do not match as shown in FIG. 4. Accordingly, the masquerade judging unit 105 determines that the images are not matched when the degree of similarity is smaller than the prescribed threshold value (No in step S108), and judges that the examining object is not attempting to do the masquerade by using the flat photograph and it is the real person (step S110).

Second Exemplary Embodiment

In the first exemplary embodiment, the examining object is picked up from different angles by prompting the picked-up object to change the posture in step S103; however, the present invention is not limited to such a case. The second exemplary embodiment of the invention shown in FIG. 5 is configured such that an image picking-up unit 202 which is similar to the image picking-up unit 201 is added, and images are picked up simultaneously from a plurality of angles different from each other.

As shown in FIG. 5, it is possible to pick up a plurality of images reflecting a stereoscopic shape by picking up the examining object from a plurality of viewpoints, without prompting the examining object to change the posture. Also, it may be configured such as: fixing the first angle and the second angle by fixing positions and directions of the image picking-up units 201 and 202; inputting the information of the first angle and the second angle into the image conversion unit 103 instead of obtaining the image conversion method from one flat plane to the other flat plane in step S105; and the image conversion unit 103 performs the processing of the image conversion based on the information.

Here, although the second exemplary embodiment shown in FIG. 5 is configured such that the image picking-up unit is added when the examining object is picked up from a plurality of angles, the present invention is not limited to such a case. For example, the examining object may be picked up from a plurality of angles by making the image picking-up unit 201 shown in FIG. 1 be movable, and causing one image picking-up unit to be moved.

Note that the masquerade detection system may be realized in such a manner as: configuring the masquerade detection system according to the exemplary embodiment of the invention as a program; and causing a computer to execute the program. In such a case, the program is stored in a recording medium and subjected to a commercial transaction.

Next, an effect of the masquerade detection device 1 will be explained.

In the case of the masquerade using the flat photograph, an image picked up from a certain angle matches with an image picked up from a different angle, by performing the image conversion from one flat plane to the other flat plane appropriately. On the other hand, in the case of the real person having an uneven shape, the images do not match by performing the image conversion from one flat plane to the other flat plane.

With the masquerade detection device 1, the image conversion unit 103 performs the image conversion from one flat plane to the other flat plane, and the masquerade judging unit 105 compares the converted image and the second angle image. Therefore, in the case of the masquerade using the flat photograph, a deformation of the image to be generated by the image conversion is not generated. By using only two images of the converted image and the second angle image and judging whether the two images match or not, the masquerade can be detected with a high degree of accuracy.

Also, the second angle image can be obtained by using the measurement device 200 only, without using an external illumination, a distance detecting device or the like. Therefore, the masquerade can be detected without using additional devices other than the image picking-up device.

Also, the examining object extracting unit 101 extracts the examining object images from the first angle image and the second angle image. Then, the image conversion unit 103 and the masquerade judging unit 105 process the examining object images. Therefore, even when the position and the size of the examining object in the picked up image are changed, or even when an object other than the examining object is present in the image, the masquerade can be detected with a high degree of accuracy.

The image conversion unit 103 acquires the converting method with which the image of the first portion of the first angle image and the image of the first portion of the second angle image are to be matched. Therefore, the masquerade can be detected with a high degree of accuracy without fixing the first angle and the second angle.

Also, since the converting method for performing the image conversion from one flat plane to the other flat plane can be obtained based on a small number of corresponding points, the processing load upon obtaining the corresponding points is small, and a highly precious conversion is possible by using corresponding points stably obtained only. Therefore, the masquerade can be detected with a high degree of accuracy with a lower processing load.

When the examining object is picked up with its posture changed so as to be able to obtain the first angle image and the second angle image, the masquerade can be detected by using the single image picking-up unit 201 only, as shown in FIG. 1, without using an additional device.

If two of the image picking-up units 201 and 202 are provided, as shown in FIG. 5, for giving the first angle image and the second angle image in advance, the image converting method for performing the image conversion from one flat plane to the other flat plane is also given in advance. Therefore, it is not required to obtain the image converting method based on the two images, and the masquerade can be detected with a lower processing load.

Further, when the image conversion unit 103 is configured so as to obtain the image converting method based on a portion other than the examining object in addition to the first portion, an error in the image conversion can be reduced, and the masquerade can be detected with a high degree of accuracy.

When the examining object is a human face, by defining a portion which can be extracted stably among portions in the face as the first portion, the first angle image and the second angle image can be corresponded with a high degree of accuracy, and the masquerade can be detected with a high degree of accuracy.

Examples of the first portions described above are referred to as follows:

(1) Center point or contour point of: both eyes; eyebrows; mouth; or nostrils (2) Both center points of eyes, and both end points of mouth (3) Both center points of eyes; center point between mouth; size of mouth; and slope of mouth The masquerade judging unit 105 compares the images containing the second portions.

Therefore, the masquerade judging unit 105 judges whether the second portions is present on a plane containing the first portion, and the masquerade using the flat photograph can be detected with a high degree of accuracy.

When the examining object is a human face, by defining a portion whose appearance significantly varies when the direction of the face changes as the second portion, the masquerade can be detected with a high degree of accuracy.

Examples of the second portions described above are referred to as follows:

(1) Facial contour (2) Nose portion (3) Cheeks between mouth and facial contour (In this case, the length of the cheeks are compared)

The image conversion unit 103 obtains a converted image which is converted in such a manner that the images containing the first portions of the first angle image and the second angle image are to be matched. Consequently, if the masquerade judging unit 105 is configured so as to compare the images of the entire examining object, it means that the masquerade judging unit 105 compares the images of the entire examining object containing the second portion, from which the first portion is eliminated, and the masquerade can be detected with a lower processing load without extracting the second portions.

While the invention has been described with reference to exemplary embodiments (and examples) thereof, the invention is not limited to these embodiments (and examples). Various changes in form and details which are understood by those skilled in the art may be made within the scope of the present invention.

REFERENCE NUMERALS

Figure 1:
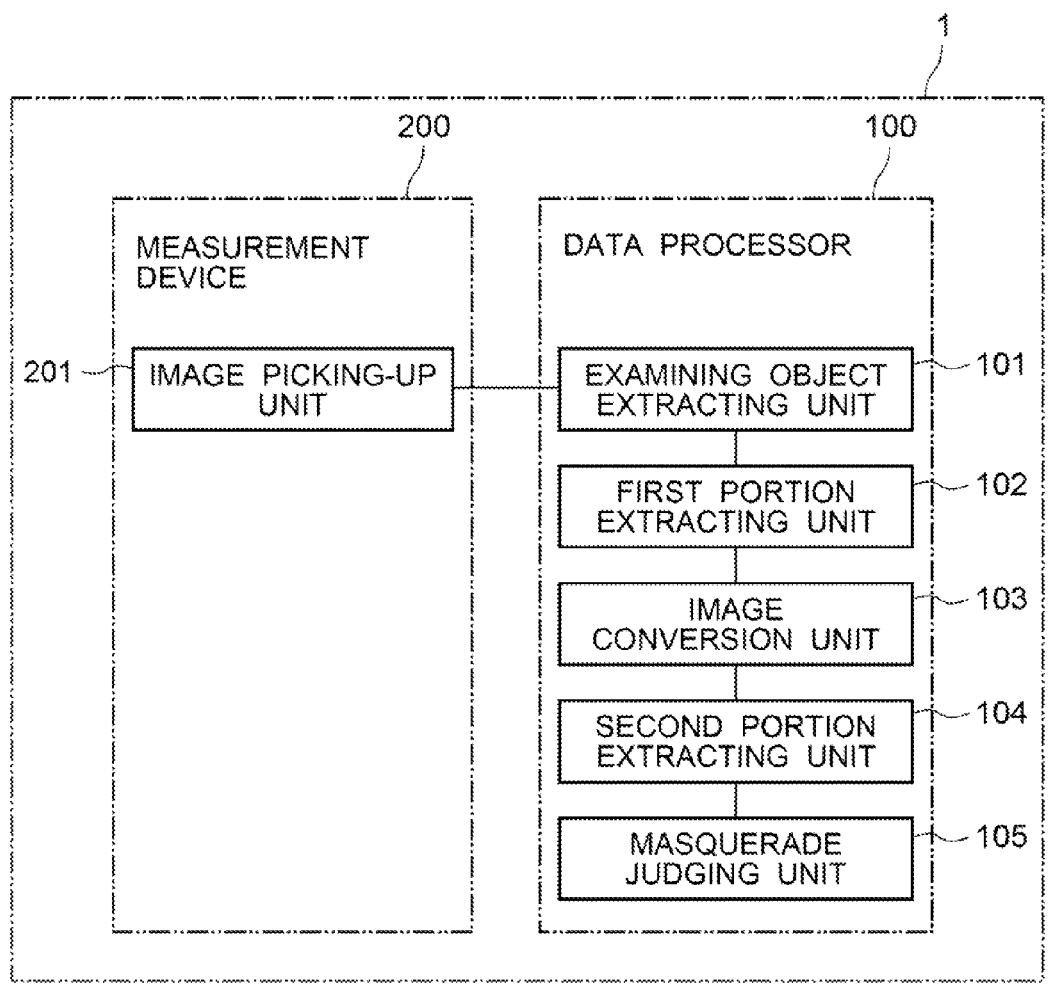
FIG. 1 is a block diagram showing a configuration of a masquerade detection system according to a first exemplary embodiment of the invention.
Figure 2:
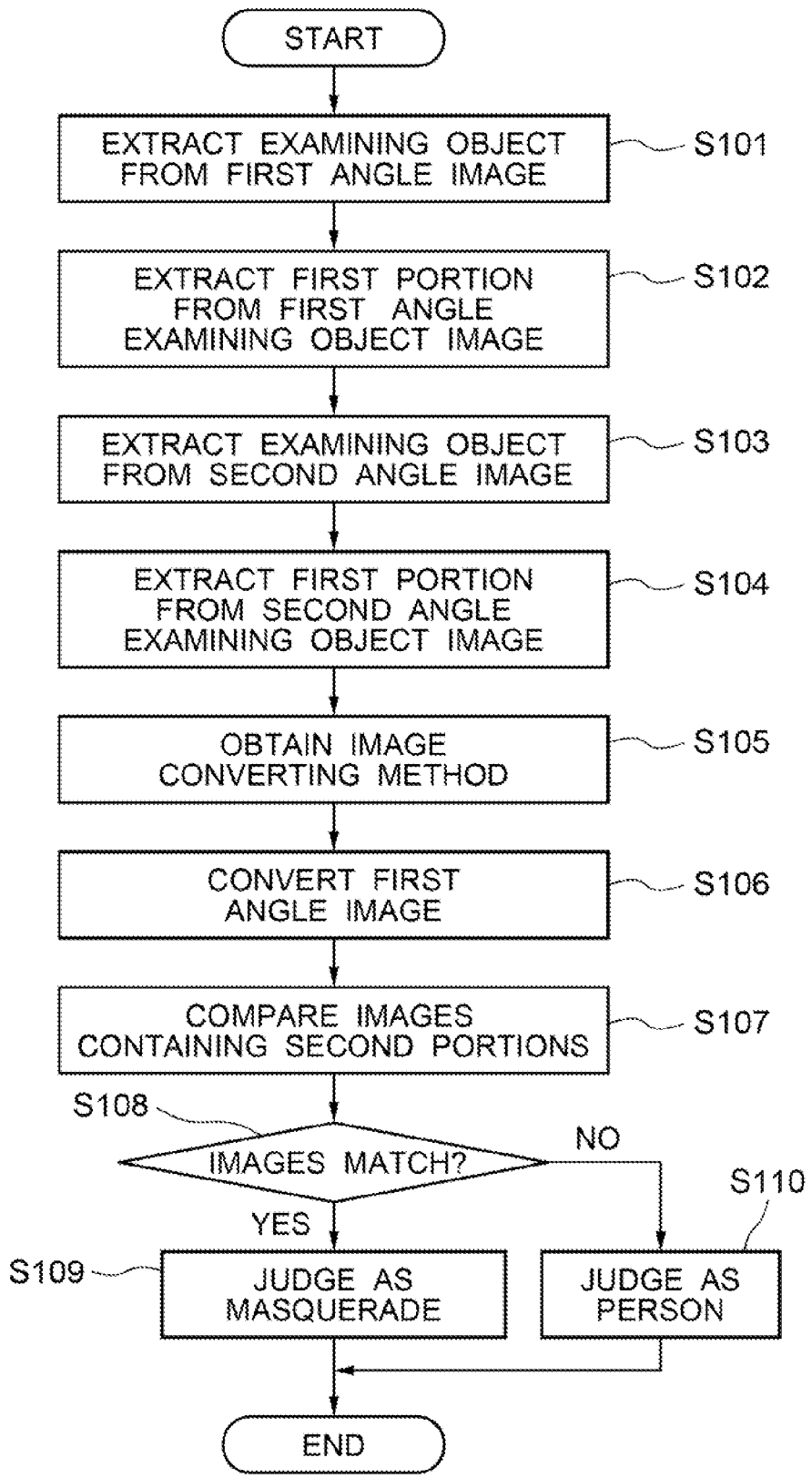
FIG. 2 is a flowchart showing an example of the detection system.
Figure 3:
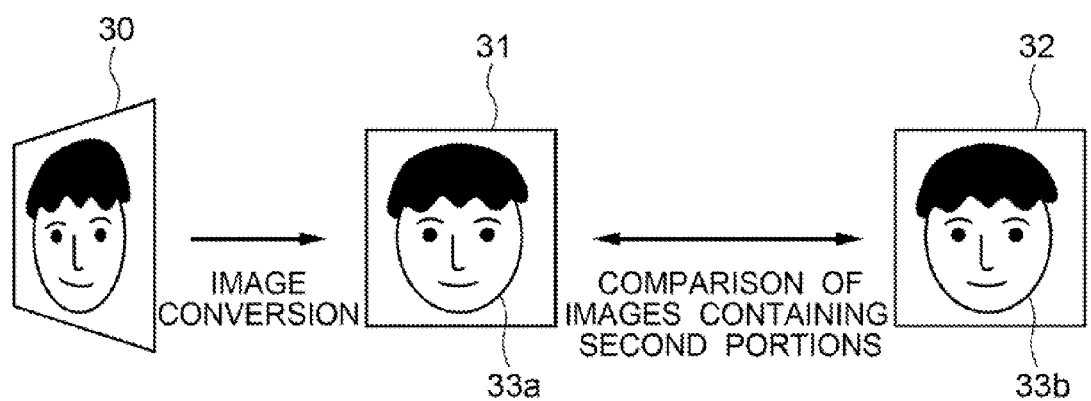
FIG. 3 is an explanatory diagram showing an example of an image conversion with respect to a masquerading image using a photograph.
Figure 4:
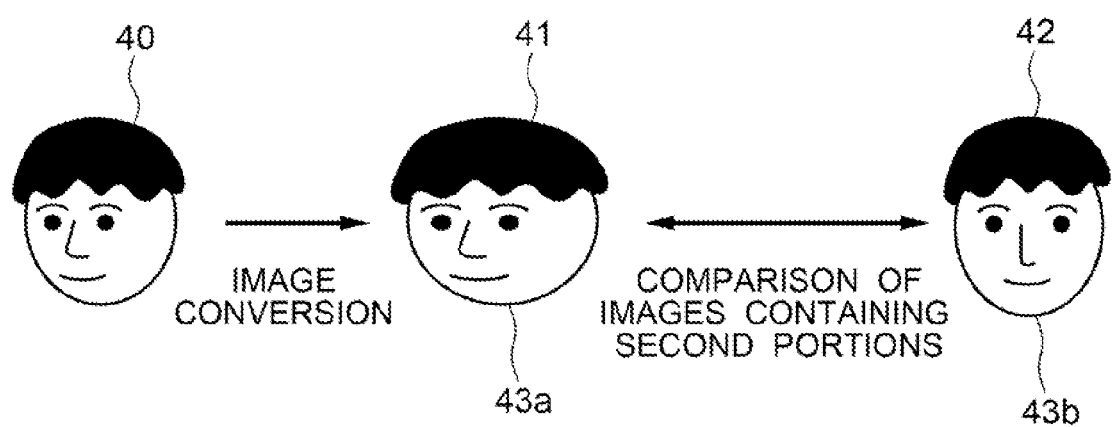
FIG. 4 is an explanatory diagram showing an example of an image conversion with respect to a facial image of a real person.
Figure 5:
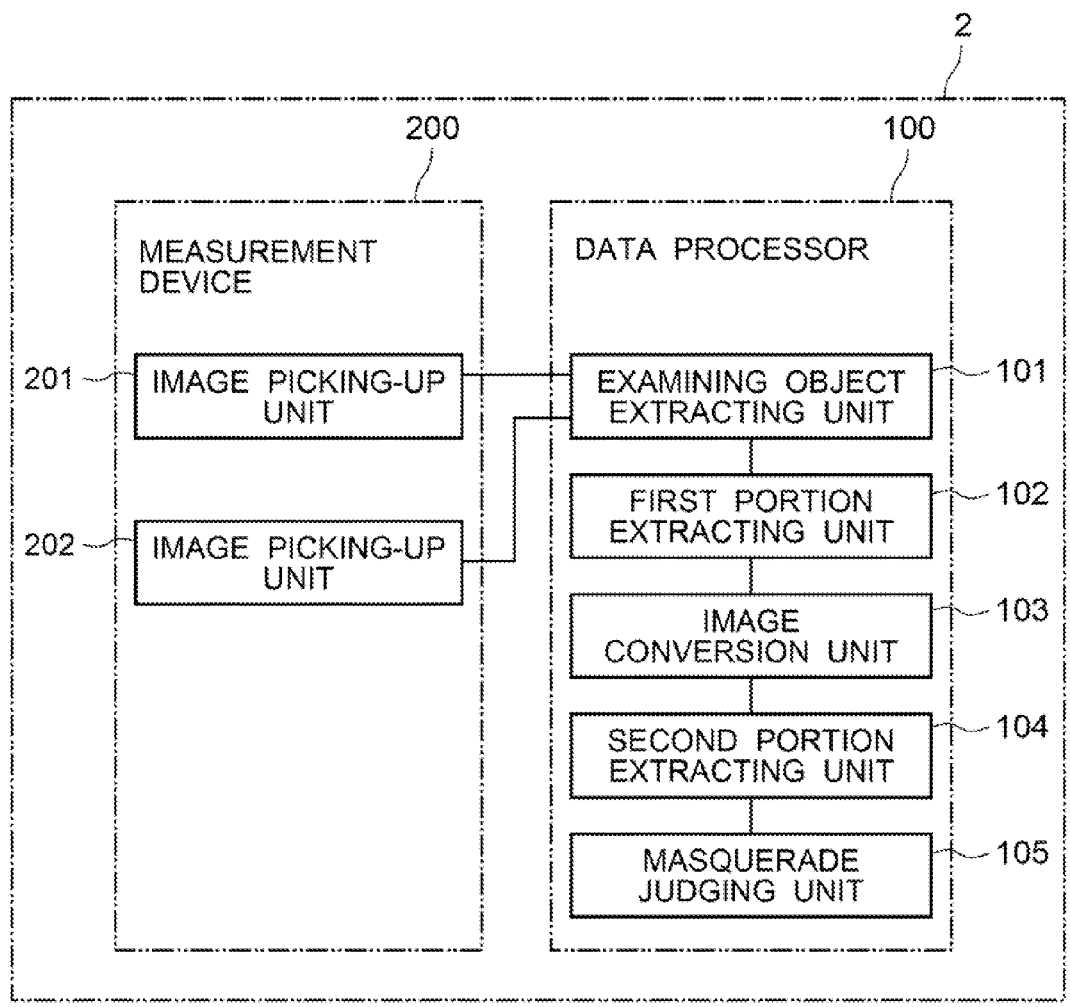
FIG. 5 is a diagram showing a configuration of a masquerade detection system according to a first exemplary embodiment of the invention.

1, 2 Masquerade detection system
100 Data processor
101 Examining object extracting unit
102 First portion extracting unit
103 Image conversion unit
104 Second portion extracting unit
105 Masquerade judging unit
200 Measurement device
201, 202 Image picking-up unit

What is claimed is:

1. A masquerade detection method for detecting a masquerade by comparing an image containing an examining object with an image, which is a target for comparison, containing an examining object, comprising:

obtaining an image converting method by comparing an image of a first portion of the examining object picked up from one angle with an image of the first portion of the examining object picked up from other angle;

based on the obtained image converting method, converting an image containing the examining object picked up from the one angle into an image of the examining object picked up from the other angle different from the one angle, by performing an image conversion from one flat plane to other flat plane; and judging the masquerade by comparing an image of a second portion different from the first portion in the converted image which is converted from one flat plane to other flat plane and an image of the second portion different from the first portion in the image containing the examining object picked up from the other angle.

2. The masquerade detection method as claimed in claim 1, comprising:

obtaining the image converting method by using the image of the first portion and an image of the portion other than the examining object when comparing the image of the first portion of the examining object picked up from the one angle with the image of the first portion of the examining object picked up from the other angle.

3. The masquerade detection method as claimed in claim 1, comprising:

using a picked up facial image as the image of the examining object.

4. The masquerade detection method as claimed in claim 1, comprising:

using a picked up image containing four or more points from among center points or contour points of: both eyes; eyebrows; a mouth; or nostrils, as the first portion image.

5. The masquerade detection method as claimed in claim 1, comprising:

using a picked up image containing both center points of eyes, and both endpoints of a mouth, as the first portion image.

6. The masquerade detection method as claimed in claim 1, comprising:
using a picked up image showing both center points of eyes; a center point of a mouth; a size of the mouth; and a slope of the mouth, as the first portion image.

7. The masquerade detection method as claimed in claim 1, comprising:
using a picked up image including a facial contour as the second portion image.

8. The masquerade detection method as claimed in claim 1, comprising:
using a picked up image including a nose as the second portion image.

9. The masquerade detection method as claimed in claim 1, comprising:
comparing the images containing the second portions by using images of entire examining object containing the second portion.

10. The masquerade detection method as claimed in claim 1, comprising:
using a picked up image containing the cheek part between the mouth and the facial contour as the image of the second portion; and
comparing the images containing the second portions by setting the length of the cheek part as a reference.

11. The masquerade detection method as claimed in claim 1, comprising:
comparing the images containing the second portions by setting a difference in the luminance values of the images as a reference.

12. The masquerade detection method as claimed in claim 1, comprising:
comparing the images containing the second portions by setting a normalized correlation value of the luminance values of the images as a reference.

13. The masquerade detection method as claimed in claim 1, comprising:
obtaining images picked up from different angles by picking up corresponding to a postural change of the examining object.

14. A masquerade detection system for detecting a masquerade by comparing an image containing an examining object with an image, which is a target for comparison, containing an examining object, comprising:
an image converting device which obtains an image converting method by comparing an image of a first portion of the examining object picked up from one angle with an image of the first portion of the examining object picked up from other angle, and based on the obtained image converting method, converts an image containing the examining object picked up from one angle into an image of the examining object picked up from other angle different from the one angle, by performing an image conversion from one flat plane to other flat plane; and
a judging device which judges the masquerade by comparing an image of a second portion different from the first portion in the converted image which is converted from one flat plane to other flat plane and an image of the second portion different from the first portion in the image containing the examining object picked up from the other angle.

15. The masquerade detection system as claimed in claim 14, wherein:
the image converting device obtains the image converting method by using the image of the first portion and an image of a portion other than the examining object when comparing the image of the first portion of the examining object picked up from the one angle with the image of the first portion of the examining object picked up from the other angle.

16. The masquerade detection system as claimed in claim 14, wherein:
the image converting device uses a picked up facial image as the image of the examining object.

17. The masquerade detection system as claimed in claim 14, wherein:
the image converting device uses a picked up image containing four or more points from among center points or contour points of: both eyes; eyebrows; a mouth; or nostrils, as the first portion image.

18. The masquerade detection system as claimed in claim 14, wherein:
the image converting device uses a picked up image containing both center points of eyes, and both endpoints of a mouth, as the first portion image.

19. The masquerade detection system as claimed in claim 14, wherein:
the image converting device uses a picked up image showing both center points of eyes; a center point of a mouth; a size of the mouth; and a slope of the mouth, as the first portion image.

20. The masquerade detection system as claimed in claim 14, wherein:
the judging device uses a picked up image including a facial contour as the second portion image.

21. The masquerade detection system as claimed in claim 14, wherein:
the judging device uses a picked up image including a nose as the second portion image.

22. The masquerade detection system as claimed in claim 14, wherein:
the judging device compares the images containing the second portions by using images of the entire examining object containing the second portion.

23. The masquerade detection system as claimed in claim 14, wherein:
the judging device uses a picked up image containing the cheek part between the mouth and the facial contour as the image of the second portion, and compares the images containing the second portions by setting the length of the cheek part as a reference.

24. The masquerade detection system as claimed in claim 14, wherein:
the judging device compares the images containing the second portions by setting a difference in the luminance values of the images as a reference.

25. The masquerade detection system as claimed in claim 14, wherein:
the judging device compares the images containing the second portions by setting a normalized correlation value of the luminance values of the images as a reference.

26. The masquerade detection system as claimed in claim 14, comprising:
a device which obtains images picked up from different angles by picking up corresponding to a postural change of the examining object.

27. A computer readable recording medium storing a masquerade detection program for controlling a detection of a masquerade by comparing an image containing an examining object with an image, which is a target for comparison, containing an examining object, causing a computer to execute:

a function of obtaining an image converting method by comparing an image of a first portion of the examining object picked up from one angle with an image of the first portion of the examining object picked up from other angle;

a function of, based on the obtained image converting method, converting an image containing the examining object picked up from the one angle into an image of the examining object picked up from the other angle different from the one angle, by performing an image conversion from one flat plane to other flat plane; and a function of judging the masquerade by comparing an image of a second portion, different from the first portion, in the converted image which is converted from one flat plane to other flat plane and an image of the second portion, different from the first portion, in the image containing the examining object picked up from the other angle.

28. The computer readable recording medium storing the masquerade detection program as claimed in claim 27, causing a computer to execute:

a function of obtaining the image converting method by using the image of the first portion and the image of a portion other than the examining object when comparing the image of the first portion of the examining object picked up from the one angle with the image of the first portion of the examining object picked up from the other angle.

29. The computer readable recording medium storing the masquerade detection program as claimed in claim 27, causing a computer to execute:

a function of obtaining the image converting method by using a picked up facial image as the image of the examining object.

30. The computer readable recording medium storing the masquerade detection program as claimed in claim 27, causing a computer to execute:

a function of obtaining the image converting method by using a picked up image containing four or more points from among center points or contour points of: both eyes; eyebrows; a mouth; or nostrils, as the first portion image.

31. The computer readable recording medium storing the masquerade detection program as claimed in claim 27, causing a computer to execute:

a function of obtaining the image converting method by using a picked up image containing both center points of eyes, and both endpoints of mouth, as the first portion image.

32. The computer readable recording medium storing the masquerade detection program as claimed in claim 27, causing a computer to execute:

a function of obtaining the image converting method by using a picked up image showing both center points of eyes; a center point of a mouth; a size of the mouth; and a slope of the mouth, as the first portion image.

33. The computer readable recording medium storing the masquerade detection program as claimed in claim 27, causing a computer to execute:

a function of judging the masquerade by using a picked up image including a facial contour as the second portion image.

34. The computer readable recording medium storing the masquerade detection program as claimed in claim 27, causing a computer to execute:

a function of judging the masquerade by using a picked up image including a nose as the second portion image.

35. The computer readable recording medium storing the masquerade detection program as claimed in claim 27, causing a computer to execute:

a function of comparing the images containing the second portions by using images of the entire examining object containing the second portion.

36. The computer readable recording medium storing the masquerade detection program as claimed in claim 27, causing a computer to execute:

a function of, by using a picked up image containing the cheek part between the mouth and the facial contour as the image of the second portion, comparing the images containing the second portions by setting the length of the cheek part as a reference.

37. The computer readable recording medium storing the masquerade detection program as claimed in claim 27, causing a computer to execute:

a function of comparing the images containing the second portions by setting a difference in the luminance values of the images as a reference.

38. The computer readable recording medium storing the masquerade detection program as claimed in claim 27, causing a computer to execute:

a function of comparing the images containing the second portions by setting a normalized correlation value of the luminance values of the images as a reference.

39. A masquerade detection system for detecting a masquerade by comparing an image containing an examining object with an image, which is a target for comparison, containing an examining object, comprising:

image converting means for obtaining an image converting method by comparing an image of a first portion of the examining object picked up from one angle with an image of the first portion of the examining object picked up from other angle, and based on the obtained image converting method, converting an image containing the examining object picked up from one angle into an image of the examining object picked up from other angle different from the one angle, by performing an image conversion from one flat plane to other flat plane; and judging means for judging the masquerade by comparing an image of a second portion different from the first portion in the converted image which is converted from one flat plane to other flat plane and an image of the second portion different from the first portion in the image containing the examining object picked up from the other angle.

* * * * *